United States Patent [19]
Williams

[11] Patent Number: 5,422,112
[45] Date of Patent: Jun. 6, 1995

[54] THICKENED COSMETIC COMPOSITIONS

[75] Inventor: Lorraine Williams, Shelton, Conn.

[73] Assignee: Chesebrough-Pond's USA Co., Division of Conopco, Inc., Greenwich, Conn.

[21] Appl. No.: 257,408

[22] Filed: Jun. 9, 1994

[51] Int. Cl.$^6$ .............................................. A61K 7/24
[52] U.S. Cl. ..................... 424/401; 424/47; 514/844; 514/938
[58] Field of Search .................. 424/401, 70, 71; 514/844, 557, 47, 938

[56] References Cited

U.S. PATENT DOCUMENTS

| | | | |
|---|---|---|---|
| 4,272,544 | 6/1981 | Cella et al. | 424/273 |
| 4,363,815 | 12/1982 | Yu et al. | 424/274 |
| 4,424,234 | 1/1984 | Alderson et al. | 424/317 |
| 4,540,567 | 9/1985 | Oneto et al. | 424/45 |

Primary Examiner—Thurman K. Page
Assistant Examiner—Sharon Howard
Attorney, Agent, or Firm—Milton L. Honig

[57] ABSTRACT

Cosmetic compositions are provided containing a thickening system that includes a heterobiopolysaccharide gum such as xanthan gum, an inorganic thickening agent such as magnesium aluminum silicate and a polyacrylamide. These compositions are particularly effective with thickening $C_1$–$C_{25}$ α-hydroxy carboxylic acids and salts thereof, especially at low pH. Furthermore, the combination thickening system functions to stabilize the compositions against phase separation.

7 Claims, No Drawings

THICKENED COSMETIC COMPOSITIONS

BACKGROUND OF THE INVENTION

1. Field of the Invention

The invention relates to improved thickening systems for cosmetic compositions, particularly those in lotion and cream form.

2. The Related Art

Aqueous cosmetic compositions often require thickeners to achieve an aesthetically pleasing viscosity. Fluids that flow with a watery consistency too rapidly run off the treated skin areas. For a cosmetic to be effective, it often must have substantivity. Thickeners provide this substantivity. Furthermore, low viscosity formulas which may be skin effective nevertheless through their wateriness signal ineffectiveness to the consumer. Products of watery consistency are also aesthetically displeasing to consumers with expectations of rich and creamy products.

Countless numbers of thickening agents are known in the literature. Perhaps this plethora intimates that not all thickening agents are equally effective for any particular type of formulation.

Indeed, there are some formulations which are extremely difficult to thicken, and even if initially thickened may have storage stability problems. Low pH systems are particularly sensitive and difficult.

Accordingly, it is an object of the present invention to provide a thickener system and thickened cosmetic compositions of sufficiently aesthetically pleasing viscosity.

It is another object of the present invention to provide thickening systems for cosmetic compositions that are effective at low pH.

It is still another object of the present invention to provide thickening systems for water and oil emulsion cosmetic compositions that also function as stabilizers preventing phase separation.

These and other objects of the present invention will more readily become apparent from the description and examples which follow.

SUMMARY OF THE INVENTION

A cosmetic composition is provided which includes:
i) from about 0.01 to 20% of a $C_1$-$C_{25}$ α-hydroxy carboxylic acid and its salts and mixtures thereof;
ii) from about 0.01 to 5% of a heterobiopolysaccharide gum;
iii) from about 0.01 to 10% of an inorganic thickening agent;
iv) from about 0.01 to 5% of a polyacrylamide; and
v) a cosmetically acceptable carrier.

DETAILED DESCRIPTION OF THE INVENTION

Now it has been discovered that a heterobiopolysaccharide gum, an inorganic thickening agent and polyacrylamide combine to form a highly effective thickening system for cosmetic compositions. This system is particularly useful for building viscosity in relatively acidic compositions, especially those containing $C_1$-$C_{25}$ α-hydroxy carboxylic acids and salts thereof. Beyond builder viscosity, the thickening system of this invention has the further advantage of stabilizing oil and water emulsions.

Accordingly, a first essential element of compositions according to the present invention is that of a heterobiopolysaccharide gum. These heterobiopolysaccharides are produced, in particular, by the fermentation of sugars by microorganisms and generally comprise glucose, mannose and glucuronic or galacturonic acid units in their structure.

Among these heterobiopolysaccharides, those more particularly preferred are the scleroglucans or the xanthan gums produced by the action of the bacterium Xanthomonas campestri and the mutants or variants thereof having a molecular weight of between 1,000,000 and 50,000,000. The xanthan gums have a viscosity of between 0.60 and 1.65 Pa s in the case of an aqueous composition containing 1% of xanthan gum, measured with a Brookfield type LVT viscometer at 60 revolutions/minute. In their structure, they comprise three different monosaccharides which are mannose, glucose and glucuronic acid. Xanthan gums are commercially available from "Keltrol" by the Kelco Division of Calgon Corporation, under the trademarks KELTROL and KELZAN.

Amounts of the heterobiopolysaccharide gum may range from about 0.001 to about 5%, preferably from about 0.1 to about 2%, optimally from about 0.2 to about 0.5% by weight.

A second essential element of compositions according to the present invention is that of an inorganic thickening agent. Most preferred is magnesium aluminum silicate, commercially available as Veegugum ® K available from the R. T. Vanderbilt Company. Amounts of the inorganic thickening agent may range from about 0.01 to about 10%, preferably from about 0.5 to about 3%, optimally from about 0.8 to about 1.2% by weight.

A third essential element of compositions according to the present invention is that of a $C_1$-$C_{25}$ polyacrylamide. The preferred polyacrylamide is available commercially under the trademark Sepigel 305 ® from Seppic, Inc., Fairfield, N.J. Small amounts of a $C_{13}$-$C_{14}$ Isoparaffin and Laureth-7 are present alongside the polyacrylamide in Sepigel 305 ®. Molecular weight of the polyacrylamide may range anywhere from 1000 up to 5 million. Preferably the polyacrylamide is a cross-linked polyacrylamide. Amounts of the polyacrylamide may range from about 0.01 to about 5%, preferably from about 0.1 to about 3%, optimally from about 0.4 to about 1% by weight.

Relative weight amounts of the heterobiopolysaccharide gum to polyacrylamide may range from about 10:1 to about 1:5, preferably from about 3:1 to about 1:3, optimally from about 1:1 to about 1:2. The relative weight amounts of heterobiopolysaccharide gum to total amount of polyacrylamide and inorganic thickening agent may range from about 10:1 to about 1:8, preferably from about 6:1 to about 1:6, optimally from about 2:1 to about 1:2.

Compositions of the present invention may include a $C_1$-$C_{25}$ α-hydroxy carboxylic acid of Formula I, having the structure:

$$R-\overset{R^1}{\underset{OH}{C}}-COOH \qquad (I)$$

wherein R and $R^1$ are H, F, Cl, Br, alkyl, aralkyl or aryl groups being saturated or unsaturated, isomeric or nonisomeric, straight or branched chain, or in cyclic form having 5 or 6 ring members, and in addition, R and R¹ may carry OH, CHO, COOH and alkoxy groups having 1 to 9 carbon atoms, the α-hydroxyacid existing as a free acid or lactone form, or in salt form with an organic amine base or an inorganic alkali, and as stereoisomers, and D, L, and DL forms when R and R¹ are not identical.

Illustrative of this group of materials are 2-hydroxyethanoic acid (glycolic acid); 2-hydroxypropanoic acid (lactic acid); 2-methyl 2-hydroxypropanoic acid (methyllactic acid); 2-hydroxybutanoic acid; 2-hydroxypentanoic acid; 2-hydroxyhexanoic acid; 2-hydroxyheptanoic acid; 2-hydroxyoctanoic acid; 2-hydroxynonanoic acid; 2-hydroxydecanoic acid; 2-hydroxyundecanoic acid; 2-hydroxydodecanoic acid (α-hydroxylauric acid); 2-hydroxytetradecanoic acid (α-hydroxymyristic acid); 2-hydroxyhexadecanoic acid (α-hydroxypalmitic acid); 2-hydroxyoctadecanoic acid (α-hydroxystearic acid); 2-hydroxyeicosanoic acid (α-hydroxyarachidonic acid); 2-phenyl 2-hydroxyethanoic acid (mandelic acid); 2,2-diphenyl 2-hydroxyethanoic acid (benzilic acid); 3-phenyl 2-hydroxypropanoic acid (phenyllactic acid); 2-phenyl 2-methyl 2-hydroxyethanoic acid (atrolactic acid); 2-(4'-hydroxyphenyl) 2-hydroxyethanoic acid; 2-(4'-chlorophenyl 2-hydroxyethanoic acid; 2-(3'-hydroxy-4'-methoxyphenyl) 2-hydroxyethanoic acid; 2-(4'-hydroxy-3'-methoxyphenyl) 2-hydroxyethanoic acid; 3-(2-hydroxyphenyl) 2-hydroxypropanoic acid; 3-(4'-hydroxyphenyl) 2-hydroxypropanoic acid; and 2-(3',4'-dihydroxyphenyl) 2-hydroxyethanoic acid.

Most preferred of this group of materials are glycolic acid, lactic acid and 2-hydroxyoctanoic acid and salts thereof. The salts may be selected from alkalimetal, ammonium and $C_1$-$C_{20}$ alkyl or alkanolammonium counterions. Levels of α-hydroxyalkanoic acids may range from about 0.01 to about 20%, preferably from about 0.2 to about 10%, optimally from about 1 to about 5% by weight.

Compositions of the present invention may either be aqueous or anhydrous. Preferably the compositions are aqueous, especially water and oil emulsions of the W/O or O/W variety. Water when present will be in amounts which may range from about 5 to about 90%, preferably from about 35 to about 65%, optimally between about 40 and 50% by weight. Advantageously the pH of such aqueous systems may range from about 8.0 down to 1.0, preferably ranging from about 6.8 to about 4, optimally between about 5.5 and 5.

Besides water, relatively volatile solvents may also be incorporated within compositions of the present invention. Most preferred are monohydric $C_1$-$C_3$ alkanols. These include ethyl alcohol, methyl alcohol and isopropyl alcohol. The amount of monohydric alkanol may range from about 5 to about 50%, preferably from about 15 to about 40%, optimally between about 25 to about 35% by weight.

Emollient materials in the form of mineral oils, silicone oils and synthetic esters may be incorporated into compositions of the present invention. Amounts of the emollients may range anywhere from about 0.1 to about 30%, preferably between about 0.5 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C.

Among suitable ester emollients are:
(1) Alkenyl or alkyl esters of fatty acids having 10 to 20 carbon atoms. Examples thereof include isopropyl palmitate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, myristyl myristate, stearyl stearate.
(5) Sterols esters, of which soya sterol and cholesterol fatty acid esters are examples thereof.

The most preferred esters are PEG-40 Stearate and isopropyl palmitate.

Fatty acids having from 10 to 30 carbon atoms may also be included in the compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be included in the compositions of this invention. The humectant aids in increasing the effectiveness of the emollient, reduces scaling, stimulates removal of built-up scale and improves skin feel. Typical polyhydric alcohols include glycerol (also known as glycerin), polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably glycerin. The amount of humectant may range anywhere from 0.5 to 30%, preferably between 1 and 15% by weight of the composition.

Collectively the water, solvents, silicones, esters, fatty acids and/or humectants are viewed as cosmetically acceptable carriers for the compositions of the invention. Total amount of carrier will range from about 1 to 99.9%, preferably from about 80 to 99% by weight.

Cosmetic compositions of the present invention may be in any form. These forms may include lotions, creams, roll-on formulations, mousses, aerosol sprays and pad-applied formulations.

Surfactants may also be present in cosmetic compositions of the present invention. Total concentration of the surfactant will range from about 0.1 to about 40%, preferably from about 1 to about 20%, optimally from about 1 to about 5% by weight of the total composition. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from about 2 to about 100 moles of ethylene oxide or propylene oxide per mole of hydrophobe; $C_2$-$C_{10}$ alkyl phenols condensed with from 2 to 20 moles of alkylene oxide; mono- and di- fatty acid esters of ethylene glycol; fatty acid monoglyceride; sorbitan, mono- and di- $C_8$-$C_{20}$ fatty acids; and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates and combinations thereof.

Sunscreen actives may also be included in compositions of the present invention. Particularly preferred are such materials as ethylhexyl p-methoxycinnamate, available as Parsol MCX, and benzophenone-3, also known as Oxybenzone. Inorganic sunscreen actives may be employed such as microfine titanium dioxide, polyethylene and various other polymers. Amounts of the sunscreen agents will generally range from about 0.1 to about 30%, preferably from about 2 to about 20%, optimally from about 4 to about 10% by weight.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition.

Minor adjunct ingredients may also be present in the cosmetic compositions. Among them may be the water-insoluble vitamins such as Vitamin A Palmitate, Vitamin E Acetate and DL-panthenol.

Colorants, fragrances, opacifiers and abrasives may also be included in compositions of the present invention. Each of these substances may range from about 0.05 to about 5%, preferably between 0.1 and 3% by weight.

The following Examples will more fully illustrate the embodiments of this invention. All parts, percentages and proportions referred to herein and in the appended claims are by weight unless otherwise indicated.

EXAMPLE 1

The following formulation is a lotion composition illustrative of the present invention.

| INGREDIENT | WT % |
|---|---|
| L-Lactic Acid | 5.68 |
| Emollients* | 5.82 |
| Glycerin USP | 5.00 |
| Potassium Hydroxide 45% | 3.20 |
| PEG-40 Stearate | 2.00 |
| Steareth-2 | 1.00 |
| Magnesium Aluminum Silicate | 1.00 |
| Stearic Acid | 0.19 |
| Fragrance | 0.08 |
| Polyacrylamide | 0.50 |
| Xanthan Gum | 0.25 |
| Disodium EDTA | 0.11 |
| Iodopropynyl Butyl Carbamate | 0.10 |
| Vitamins** | 0.02 |
| Deionized Water | Balance |

*Includes Isopropyl Palmitate, Cetyl Alcohol, Dimethicone, Mineral Oil, Soya Sterol, Lecithin and Simethicone.
**Includes Tocopheryl Acetate and Retinyl Palmitate.

EXAMPLE 2

This Example illustrates the phase stability imparted by the thickening system according to the present invention. For these comparative experiments, a base formula was employed whose components are listed under Table I. Compositions A through I were then prepared by incorporating the thickeners of Table II into the base formula.

TABLE I

| Base Formula* | |
|---|---|
| COMPONENT | WEIGHT % |
| Lactic Acid | 5.68 |
| Glycerin | 5.00 |
| Emollients** | 3.82 |
| Potassium Hydroxide (45% Sol.) | 3.20 |
| PEG-40 Stearate | 2.00 |
| Steareth-2 | 1.00 |
| Stearic Acid | 0.19 |
| Fragrance | 0.08 |
| Disodium EDTA | 0.11 |
| Glydant Plus | 0.10 |
| Vitamins*** | 0.02 |
| Water | Balance |

*pH 3.8–4.0
**Includes Cetyl Alcohol, Isopropyl Palmitate, Soya Sterol and Lecithin.
***Includes Tocopheryl Acetate and Retinyl Palmitate.

TABLE II

| Identity of Thickeners and Performance | | | | | | | | | |
|---|---|---|---|---|---|---|---|---|---|
| COMPONENT | A | B | C | D | E | F | G | H | I |
| Xanthan Gum | 0.25 | — | 0.25 | 0.25 | — | — | — | 0.25 | 0.0625 |
| Magnesium Aluminum Silicate | 1.0 | 1.0 | — | 1.0 | — | — | 1.0 | — | 0.25 |
| Polyacrylamide | 0.5 | 0.5 | 0.5 | — | — | 0.5 | — | — | 0.5 |

Physical Properties of Emulsion
A: Stable
B: Separated
C: Clear separation lower half of lotion
D: Unstable emulsion
E: Large separation
F: Cloudy separation
G: Cloudy separation
H: Very large separation
I: ⅓ of jar separated As can be seen from the results in Table II, only composition A, according to the present invention, provided a stable emulsion. When either xanthan gum, magnesium aluminum silicate or polyacrylamide were deleted, the emulsion separated or at least became unstable. See compositions B, C and D, respectively.

The foregoing description and Examples illustrate selected embodiments of the present invention. In light thereof, various modifications will be suggested to one skilled in the art, all of which are within the spirit and purview of this invention.

What is claimed is:

1. A cosmetic composition comprising:
   i) from about 0.01 to 20% of a $C_2$-$C_{25}$ α-hydroxy carboxylic acid and its salts and mixtures thereof;
   ii) from about 0.1 to 2% of a xanthan gum;
   iii) from about 0.5 to 3% of a magnesium aluminum silicate;
   iv) from about 0.1 to 5% of a polyacrylamide; and v) a cosmetically acceptable carrier.

2. A composition according to claim 1 wherein the $C_2$-$C_{25}$ α-hydroxy carboxylic acid is selected from the group consisting of glycolic acid, lactic acid, 2-hydroxy octanoic acid and combinations thereof.

3. A composition according to claim 1 wherein the xanthan gum is present in an amount from about 0.1 to about 0.5% by weight.

4. A composition according to claim 1 wherein the magnesium aluminum silicate is present in an amount from about 0.5 to about 1.2% by weight.

5. A composition according to claim 1 wherein the polyacrylamide is present in an amount from about 0.1 to about 1% by weight.

6. A composition according to claim 1 wherein the cosmetically acceptable carrier is present in an amount from about 1 to 99% by weight.

7. A composition according to claim 1 wherein the carrier includes an aqueous system with a pH ranging from 6.8 down to 1.0.

* * * * *